(12) United States Patent
Gemborys et al.

(10) Patent No.: US 10,335,573 B2
(45) Date of Patent: Jul. 2, 2019

(54) INTRAPERITONEAL CHEMOTHERAPY MEDICAL DEVICES, KITS, AND METHODS

(71) Applicant: Cook Medical Technologies LLC, Bloomington, IN (US)

(72) Inventors: Colleen Gemborys, Bloomington, IN (US); Steve L. Pendleton, Spencer, IN (US); John Deis, Union, KY (US); Josh Haines, West Chester, OH (US); Nathan Steinbrunner, Versailles, OH (US); Louis Curtis, Louisville, KY (US)

(73) Assignee: Cook Medical Technologies LLC, Bloomington, IN (US)

( * ) Notice: Subject to any disclaimer, the term of this patent is extended or adjusted under 35 U.S.C. 154(b) by 565 days.

(21) Appl. No.: 14/956,790

(22) Filed: Dec. 2, 2015

(65) Prior Publication Data

US 2017/0157359 A1    Jun. 8, 2017

(51) Int. Cl.
*A61M 25/00*    (2006.01)
*A61B 17/34*    (2006.01)
(Continued)

(52) U.S. Cl.
CPC ..... *A61M 25/0032* (2013.01); *A61B 17/3423* (2013.01); *A61F 7/12* (2013.01);
(Continued)

(58) Field of Classification Search
CPC .. A61M 1/1629; A61M 11/0045; A61M 5/44; A61M 25/003; A61M 25/0032;
(Continued)

(56) References Cited

U.S. PATENT DOCUMENTS 4,351,342 A * 9/1982 Wiita ................ A61M 25/1002
604/101.05
5,215,993 A    6/1993 Schildknecht et al.
(Continued)

FOREIGN PATENT DOCUMENTS

WO    WO0010494 A1    3/2000
WO    WO03033045 A3    4/2003
(Continued)

OTHER PUBLICATIONS

Nagler, A., et al., "Halofuginone—an Inhibitor of Collagen Type I Synthesis—Prevents Postoperative Formation of Abdominal Adhesions," Anna. of Surg., vol. 227, No. 4, pp. 575-582, Nov. 1997.
(Continued)

*Primary Examiner* — Nathan R Price
*Assistant Examiner* — John A Doubrava
(74) *Attorney, Agent, or Firm* — Buchanan Van Tuinen LLC

(57) ABSTRACT

Medical devices useful in the delivery of chemotherapeutic agents, kits and methods are described. An example catheter comprises an elongate member having an elongate member proximal end, an elongate member distal end, and an elongate member main body extending between the elongate member proximal end and the elongate member distal end. The elongate member main body defines an elongate member circumferential wall, first, second, and third openings on the elongate member proximal end, a first heating lumen extending from the first opening toward the elongate member distal end, a second heating lumen extending from the second opening toward the elongate member distal end, and a treatment lumen extending from the third opening toward the elongate member distal end. The treatment lumen comprises a blind passage. The elongate member circumferential wall defines a plurality of passageways providing fluid
(Continued)

communication between the treatment lumen and an environment external to the catheter.

11 Claims, 9 Drawing Sheets

(51) Int. Cl.
  *A61M 5/00* (2006.01)
  *A61M 25/01* (2006.01)
  *A61M 39/20* (2006.01)
  *A61F 7/12* (2006.01)
(52) U.S. Cl.
  CPC .......... *A61M 5/002* (2013.01); *A61M 25/003* (2013.01); *A61M 25/0043* (2013.01); *A61M 25/01* (2013.01); *A61M 39/20* (2013.01); *A61F 2007/126* (2013.01); *A61M 25/0069* (2013.01); *A61M 2025/006* (2013.01); *A61M 2025/0018* (2013.01); *A61M 2025/0037* (2013.01); *A61M 2205/36* (2013.01); *A61M 2205/586* (2013.01)
(58) Field of Classification Search
  CPC ...... A61M 2025/0037; A61M 25/0015; A61M 25/007; A61M 2205/36; A61M 2205/366
  See application file for complete search history.

(56) References Cited

U.S. PATENT DOCUMENTS

| | | | |
|---|---|---|---|
| 6,159,488 A | 12/2000 | Nagler et al. | |
| RE37,828 E | 9/2002 | Pines et al. | |
| 6,562,829 B1 | 5/2003 | Pines et al. | |
| 6,645,233 B1* | 11/2003 | Ayers | A61F 7/123 607/105 |
| RE39,096 E | 5/2006 | Pines et al. | |
| 8,092,541 B2 | 1/2012 | Peckham | |
| 8,529,819 B2 | 9/2013 | Ostapoff et al. | |
| 8,668,703 B2 | 3/2014 | Sullivan et al. | |
| 8,871,721 B2 | 10/2014 | Kuo et al. | |
| 8,883,183 B2 | 11/2014 | Sullivan et al. | |
| 8,883,190 B2 | 11/2014 | Hodges et al. | |
| 9,034,042 B2 | 5/2015 | Peckham | |
| 9,192,710 B2 | 11/2015 | Feng | |
| 2004/0171627 A1 | 9/2004 | Nagler et al. | |
| 2004/0186538 A1 | 9/2004 | Eshel | |
| 2005/0222182 A1 | 10/2005 | Yarkoni et al. | |
| 2006/0009475 A1 | 1/2006 | Pines et al. | |
| 2006/0194822 A1 | 8/2006 | Nagler et al. | |
| 2006/0258692 A1 | 11/2006 | Pines et al. | |
| 2006/0293351 A1 | 12/2006 | Pines et al. | |
| 2007/0010538 A1 | 1/2007 | Pines et al. | |
| 2007/0160640 A1 | 7/2007 | Jang et al. | |
| 2008/0133027 A1 | 6/2008 | Hodges | |
| 2009/0226500 A1 | 9/2009 | Avelar et al. | |
| 2011/0098683 A1* | 4/2011 | Wiita | A61M 25/0069 604/544 |
| 2011/0212165 A1 | 9/2011 | Erez et al. | |
| 2011/0263532 A1 | 10/2011 | Keller et al. | |
| 2011/0293691 A1 | 12/2011 | Weber et al. | |
| 2014/0155965 A1* | 6/2014 | Kulstad | A61F 7/12 607/105 |
| 2014/0288102 A1 | 9/2014 | Jaidane | |
| 2015/0025015 A1 | 1/2015 | Tomblyn et al. | |
| 2015/0086627 A1 | 3/2015 | Bush et al. | |

FOREIGN PATENT DOCUMENTS

| | | |
|---|---|---|
| WO | WO2006055780 A2 | 5/2006 |
| WO | WO2010019210 | 2/2010 |
| WO | WO2013063435 | 5/2013 |
| WO | WO2013149148 | 10/2013 |

OTHER PUBLICATIONS

White, A., et al., "Intranasal adhesion formation following surgery for chronic nasal obstruction," Clinic. Otolaryng., vol. 13, No. 2, pp. 139-143, Apr. 1988.
Ward, B.C., et al., "Abdominal Adhesions: Current and Novel Therapies," Jour. of Surg. Resea., vol. 165, No. 1, pp. 91-111, Jul. 2009.
Levine, E.A., et al., "Intraperitoneal Chemotherapy for Peritoneal Surface Malignancy: Experience with 1,000 Patients," Journ. of the Am. Coll. of Surg., vol. 218, No. 4, pp. 573-585, Dec. 2013.
Zcharia, E., et al., "Inhibition of matrix metalloproteinase-2 by halofuginone is mediated by the Egr1 transcription factor," Anti-Canc. Dru., vol. 23, No. 10, pp. 1022-1031, Jul. 2012.
F. Roviello, S. Caruso, et al., "Treatment of peritoneal carcinomatosis with cytoreductive surgery and hyperthermic intraperitoneal chemotherapy: State of the art and future developments," Surg. Oncol., vol. 20, No. 1, pp. e38-e54. Mar. 2011.
H. B. Koon, B. Fingleton, et al., "Phase II AIDS malignancy consortium trial of topical halofuginone in AIDS-related Kaposi's sarcoma," J. Acquir Immune Defic. Syndr., vol. 56, No. 1, pp. 64-68. Jan. 2011.
M. Elkin, H. Q. Miao, et al., "Halofuginone: a potent inhibitor of critical steps in angiogenesis progression," Faseb J., vol. 14, No. 15, pp. 2477-2485. Dec. 2000.
M. Elkin, R. Reich, et al., "Inhibition of Matrix Metalloproteinase-2 Expression and Bladder Carcinoma Metastasis by Halofuginone," Clin. Canc. Res., vol. 5, pp. 1982-1988, Aug. 1999.
M. Pines and A. Nagler, "Halofuginone: A Novel Antifibrotic Therapy," Gen. Pharmac., vol. 30, No. 4, pp. 445-450, 1998.
M. Pines and I. Spector, "Halofuginone—The Multifaceted Molecule," Molecules, vol. 20, No. 1, pp. 573-594, Jan. 2015.
M. S. Sundrud, S. B. Koralov, et al., "Halofuginone Inhibits TH17 Cell Differentiation by Activating the Amino Acid Starvation Response," Science, vol. 1, No. 1, pp. 1334-1338, Jun. 2009.
N. Martin-Orozco, P. Muranski, et al., "T Helper 17 Cells Promote cytotoxic T Cell Activation in Tumor Immunity," Immunity, vol. 31, No. 5, pp. 787-798. Nov. 2009.
N. P. McLaughlin, P. Evans et al., "The chemistry and biology of febrifugine and halofuginone," Bioorg. & Med. Chem., vol. 22, No. 7, pp. 1993-2004. Apr. 2014.
R. Abramovitch, A. Itzik, et al., "Halofuginone Inhibits Angiogenesis and Growth in Implanted Metastatic Rat Brain Tumor Model—an MRI study," Neopla. vol. 6, No. 5, pp. 480-489. Oct. 2004.
R. G. Coelho Junior, F. H. Brandao, et al., "Frequency of Nasal Synechia after Septoplasty with Turbinectomy with or without the Use of Nasal Splints," Intl. Arch. Otorhinolaryngol., vol. 12, No. 1, pp. 24-27. Jan. 2008.
S. Washburn, J. L. Jennell, et al., "Halofuginone- and Chitosan-Coated Amnion Membranes Demonstrate Improved Abdominal Adhesion Prevention," TheScientificWorldJou., vol. 10, pp. 2362-2366. Dec. 2010.
T. D. Yan, "Peritoneal Carcinomatosis of Colorectal Origin: Standard of Care," Anna. of Surg., vol. 244, No. 4, pp. 632-633. Oct. 2006.
T. L. Keller, D. Zocco, et al., "Halofuginone and other febrifugine derivatives inhibit prolyl-tRNA synthetase," Nature Chem. Bio., vol. 8, pp. 311-317. Feb. 2012.
T. L. McGaha, R.G. Phelps et al., "Halofuginone, an Inhibitor of Type-I Collagen Synthesis and Skin Sclerosis, Blocks Transforming-Growth-Factor-β-Mediated Smad3 Activation in Fibroblasts," J. Invest. Derm., vol. 118, pp. 461-470, Nov. 2001.
T. Singh, H. Lade, et al., "Role of Mitomycin-C in Prevention of Post Operative Adhesions After Endoscopic Sinus Surgery—A Prospective Study," Ind. J. Otolar. He. Ne. Surg., vol. 63, No. 3, pp. 249-254, Sep. 2011.
Cell Signaling Technology, "TGF-B/Smad Signaling Pathway," cellsignal.com, created Jan. 2003, http://www.cellsignal.com/common/content/content.jsp?id=pathways-tgfb.
Living Well Fitness Blog, Chart, Livingwellfitnessblog.com, https://livingwellnessblog.files.wordpress.com/2012/10/t-cell-subsets.png.

(56) References Cited

OTHER PUBLICATIONS

National Institute of Diabetes and Digestive and Kidney Diseases, "Abdominal Adhesions," niddk.nih.gov, created Sep. 2013, http://www.niddk.nih.gov/health-information/health-topics/digestive-diseases/abdominal-adhesions/Pages/facts.aspx#what.

WebMD, "Allergies Health Center," webmd.com, last updated Nov. 14, 2014, http://www.webmd.com/allergies/tc/removal-of-nasal-adhesions-surgery-overview.

Sigma-Aldrich, "Safety Data Sheet," sidmaaldrich.com, last revised Aug. 1, 2014, http://www.sigmaaldrich.com/MSDS/MSDS/DisplayMSDSPage.do?country=US&language=en&productNumber=32481&brand=FLUKA&PageToGoToURL=http%3A%2F%2Fwww.sigmaaldrich.com%2Fcatalog%2Fproduct%2Ffluka%2F32481%3Flang%3Den.

The European Agency for the Evaluation of Medicinal Products, "Halofuginone: Summary Report (2)," www.ema.europa.eu, Jun. 2000, http://www.ema.europa.eu/docs/en_GB/document_library/Maximum_Residue_Limits_-_Report/2009/11/WC500014386.pdf.

Paul Rohricht, et al., "Executive Summary," Applied Catheter Technologies, Oct. 2013, http://www.slideshare.net/paulrohrichtact/applied-catheter-technologies-inc.

Clinical Trials, "Safety, Tolerability, and Pharmacokinetics of Single and Multiple Doses of HT-100 in Duchenne Muscular Dystrophy," clinicaltrials.gov, last updated Dec. 29, 2015, https://clinicaltrials.gov/ct2/show/NCT01847573.

Marc B. Blaustein, "HT-100: Patient-Partnered Drug Development for DMD," Parent Project Muscular Dystrophy Connect Conference 2012, Jun. 30, 2012, http://videos.parentprojectmd.org/conference12/PDF/Blaustein_Halo.pdf.

Orpha, "Halofuginone hydrobromide," orpha.net, last updated Jan. 21, 2016, http://www.orpha.net/consor/cgi-bin/OC_Exp_php?Ing=EN&Expert=84314.

FDA, "NADA 140-340 Lincomix, Stenorol—original approval," fda.gov, last updated Oct. 15, 2015, http://www.fda.gov/AnimalVeterinary/Products/ApprovedAnimalDrugProducts/FOIADrugSummaries/UCM049810.

European Patent Office, Extended European Search Report, dated Apr. 11, 2017.

European Patent Office. "Examination Report," dated Aug. 24, 2018.

* cited by examiner

INTRAPERITONEAL CHEMOTHERAPY MEDICAL DEVICES, KITS, AND METHODS

FIELD

The disclosure relates generally to the field of medical devices. More particularly, the disclosure relates to the field of medical devices useful in the provision of chemotherapy to patients. Particular embodiments relate to medical devices useful in the delivery of chemotherapeutic agents, kits useful in the provision of chemotherapeutic treatment, and methods of providing intraperitoneal chemotherapeutic treatment.

BACKGROUND

Peritoneal carcinomatosis is a condition characterized by the presence of multiple cancerous masses within the lining of the abdominal cavity. It is primarily caused by metastatic colorectal, ovarian, gastric, and appendicular cancers. Current treatments for peritoneal carcinomatosis include cytoreductive surgery (CRS) followed by Hyperthermic Intraperitoneal Chemotherapy (HIPEC). In this regimen, abdominal surgery is performed to remove visible masses. Subsequently, a heated chemotherapeutic solution, typically a chemotherapeutic agent and saline, is introduced into and circulated within the abdominal cavity to kill any remaining cancerous cells. Postoperative Intraperitoneal Chemotherapy (EPIC) can be performed following surgery, either in addition to or in place of the HIPEC procedure. A combination of CRS and HIPEC and/or EPIC can extend a patient's survival and recent studies suggest that repeated procedures may result in even greater survival benefits.

Repeat HIPEC and/or EPIC procedures are frequently complicated, unfortunately, by post-surgical formation of adhesions throughout the abdominal cavity. Adhesions are bands of fibrous tissue that begin forming between tissues and organs immediately following surgery. Adhesion formation is typically complete within a week, but the adhesions formed following a surgical procedure continue to become more dense and even become vascularized over months following surgery. The formation of adhesions following CRS can negatively impact the effectiveness of HIPEC and/or EPIC procedures because the adhesions can effectively mask abdominal tissue, blocking the chemotherapeutic solution from reaching all surfaces within the abdominal cavity. The adhesions can even hinder subsequent surgical procedures, including additional CRS procedures.

Widespread use of HIPEC and/or EPIC procedures has also been hindered by the lack of medical devices specifically designed and developed for these procedures. While conventional medical devices have been used in these procedures, they lack structure and function specifically tailored to the unique needs and demands of HIPEC/EPIC procedures.

A need remains, therefore, for new and useful intraperitoneal chemotherapy medical devices, kits, and methods.

BRIEF SUMMARY OF SELECTED EXAMPLES

Medical devices useful in the provision of chemotherapeutic treatment are provided, including catheters useful in the provision of HIPEC, EPIC and other procedures. An example catheter comprises an elongate member having an elongate member proximal end, an elongate member distal end, and an elongate member main body extending between the elongate member proximal end and the elongate member distal end, the elongate member main body defining an elongate member circumferential wall, first, second, and third openings on the elongate member proximal end, a first heating lumen extending from the first opening toward the elongate member distal end, a second heating lumen extending from the second opening toward the elongate member distal end, and a treatment lumen extending from the third opening toward the elongate member distal end.

In example catheters, the elongate member distal end defines a fourth opening and the treatment lumen extends from the third opening to the fourth opening. In other example catheters, the treatment lumen comprises a blind passage and the elongate member circumferential wall defines a plurality of passageways providing fluid communication between the treatment lumen and an environment external to the catheter.

Kits useful in the provision of chemotherapeutic treatment are provided, including kits useful in the provision of HIPEC and/or EPIC. An example kit comprises a catheter according to an embodiment and an abdominal access port defining first and second engaging members adapted to engage opposing surfaces of an abdominal wall of a patient and a working lumen adapted to receive the catheter.

Another example kit comprises a catheter according to an embodiment, an abdominal access port defining first and second engaging members adapted to engage opposing surfaces of an abdominal wall of a patient and a working lumen adapted to receive the catheter, and a second catheter.

In example kits, the second catheter contains halofuginone. In other example kits, a storage vessel containing halofuginone is included.

Another example kit comprises a catheter according to an embodiment, an abdominal access port defining first and second engaging members adapted to engage opposing surfaces of an abdominal wall of a patient and a working lumen adapted to receive the catheter; a second catheter adapted to remove fluid from an abdominal cavity of a patient; and a third catheter.

In example kits, the third catheter contains halofuginone. In other example kits, a storage vessel containing halofuginone is included.

Methods of providing intraperitoneal chemotherapeutic treatment are provided. An example method comprises establishing an opening in an abdominal wall of said patient; securing an abdominal access port to the abdominal wall of said patient to establish an access passageway through the opening; passing the distal end of a catheter through the passageway, the catheter comprising an elongate member having an elongate member proximal end, an elongate member distal end, and an elongate member main body extending between the elongate member proximal end and the elongate member distal end, the elongate member main body defining an elongate member circumferential wall, first, second, and third openings on the elongate member proximal end, a first heating lumen extending from the first opening toward the elongate member distal end, a second heating lumen extending from the second opening toward the elongate member distal end, and a treatment lumen extending from the third opening toward the elongate member distal end; introducing a heated fluid through the first heating lumen; withdrawing the heated fluid through the second heating lumen; introducing a chemotherapeutic solution into the treatment lumen; stopping the introducing a chemotherapeutic solution into the treatment lumen; and withdrawing the distal end of the catheter from the passageway.

Example methods also comprise removing the chemotherapeutic solution from the abdominal cavity of said patient.

Example methods also comprise introducing halofuginone into the abdominal cavity of said patient.

Figure 1:
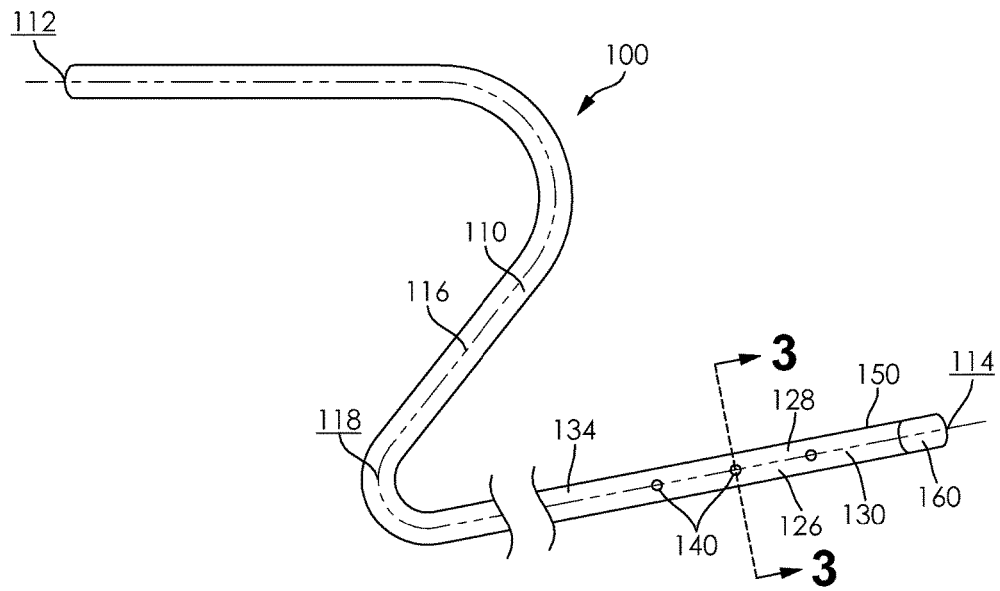
FIG. 1 is a perspective view of an example catheter.

Additional understanding of these examples and the scope of the claimed invention can be obtained with review of the drawings and the detailed description of selected examples.

DETAILED DESCRIPTION OF SELECTED EXAMPLES

The following detailed description and the appended drawings describe and illustrate various example medical devices useful in the delivery of chemotherapeutic agents, example kits useful in the provision of chemotherapeutic treatment, and example methods of providing intraperitoneal chemotherapeutic treatment. The description and illustration of these examples are provided to enable one skilled in the art to make and use a medical device and kit and to practice a method of providing intraperitoneal chemotherapeutic treatment. They are not intended to limit the scope of the claims in any manner.

As used herein, the term "attached" refers to a fixed, releasable, or integrated association of two or more items. Thus, the term includes releasably attached and fixedly attached associations between two referenced items.

As used herein, the terms "proximal end" and "distal end" refer to opposing terminal surfaces of a referenced item.

As used herein, the term "inner diameter" refers to the length of a straight line passing from a point on an inner surface of a referenced item, through a point on the longitudinal axis of the referenced item, and to an opposing or substantially opposing point on the inner surface of the referenced item.

As used herein, the term "body cavity" refers to any cavity within the body of an animal. The abdominal cavity is an example body cavity.

As used herein, the term "plurality" refers to a number of the referenced items that is greater than one referenced item. Thus, the term includes two, three, and more than three of the referenced items.

As used herein, the term "animal" includes human and other mammals.

FIGS. 1 through 3, 5 and 6 illustrate an example catheter 100 useful in the provision of HIPEC and EPIC to a patient, such as an animal. Catheter 100 comprises an elongate member 110 having an elongate member proximal end 112, an elongate member distal end 114, and an elongate member main body 116 extending between the elongate member proximal end 112 and the elongate member distal end 114. The elongate member main body 116 defines an elongate member circumferential wall 118, first 120, second 122, and third 124 openings on the elongate member proximal end 112, a first heating lumen 126 extending from the first opening 120 toward the elongate member distal end 114, a second heating lumen 128 extending from the second opening 122 toward the elongate member distal end 114, and a treatment lumen 130 extending from the third opening 124 toward the elongate member distal end 114.

The elongate member circumferential wall 118 can have any suitable structural configuration. Examples of suitable structural configuration include a circular circumferential wall, a substantially circular circumferential wall, an ovoid circumferential wall, a substantially ovoid circumferential wall, a faceted circumferential wall, and any other suitable structural configuration. In the illustrated example, the elongate member circumferential wall 118 is a faceted circumferential wall comprising a series of faceted surfaces 119, each of which extends substantially the same length along a portion of the circumference of the elongate member main body 116. The inclusion of a series of faceted surfaces 119 is considered advantageous at least because it facilitates handling of the catheter 100.

Each of the first 120, second 122, and third 124 openings can have any suitable size, shape and configuration.

Figure 2:
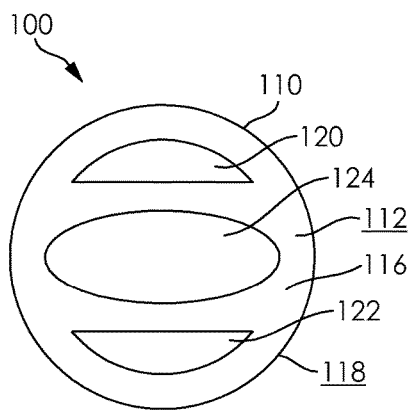
FIG. 2 is an end view of the example catheter illustrated in FIG. 1. The proximal end of the catheter is illustrated.
Figure 3:
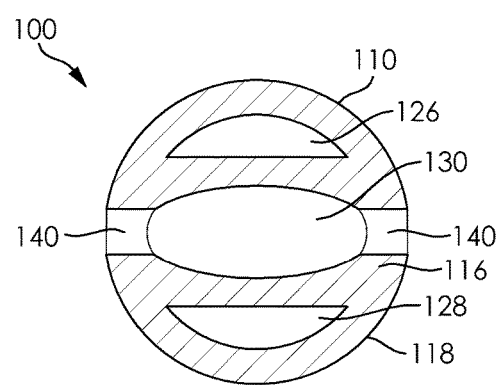
FIG. 3 is a sectional view of the catheter illustrated in FIG. 1, taken along line 3-3.

Each of the first heating lumen, 126, second heating lumen 128, and treatment lumen 130 can have any suitable size, shape, arrangement and configuration. As best illustrated in FIGS. 2 and 3, an arrangement in which the treatment lumen 130 is disposed between the heating lumens 126, 128 along a lengthwise axis of the elongate member 110 is considered advantageous at least because it facilitates efficient heating of fluid within the treatment lumen 130. Furthermore, also as best illustrated in FIGS. 2 and 3, inclusion of a treatment lumen 130 having a generally ovoid cross-sectional shape and heating lumens 126, 128 that each has a semi-ovoid cross-sectional shape is considered advantageous at least because this arrangement and configuration provides a balance between performance and manufacturability.

In the example catheter 100 illustrated in FIGS. 1 through 3, 5 and 6, the treatment lumen 130 extends along only a portion of the axial length of the elongate member 110. Thus, the treatment lumen 130 extends from the third opening 124 to a point proximal to the elongate member distal end 114. As a result, in the example catheter 100, the treatment lumen 130 comprises a blind passage having only one opening on the lengthwise axis of the elongate member 110.

In the illustrated example, the elongate member circumferential wall 118 defines a plurality of passageways 140 that individually provide fluid communication between the treatment lumen 130 and an environment external to the catheter. While the illustrated embodiment includes a plurality of passageways 140, it is noted that only one or two passageways can be included in a catheter according to a particular embodiment. Indeed, any suitable number of passageways can be included. Furthermore, the passageways in a catheter according to a particular embodiment can have any suitable size, shape, configuration, arrangement, and location. The number, size, shape, configuration, arrangement, and location of passageways included in a catheter according to a particular embodiment can be selected a skilled artisan based on various considerations, including the nature of the body cavity within which the catheter is intended to be used, the treatment agent being used, and other considerations. The inventors have determined that a plurality of passageways that comprises opposably positioned series of passageways is suitable for catheters intended to be used in abdominal cavity at least because this location and arrangement of passageways facilitates distribution and removal of the treatment agent(s) used in a particular treatment and decreases the likelihood that multiple passageways would be obstructed during delivery and removal of the treatment agent(s).

Figure 4:
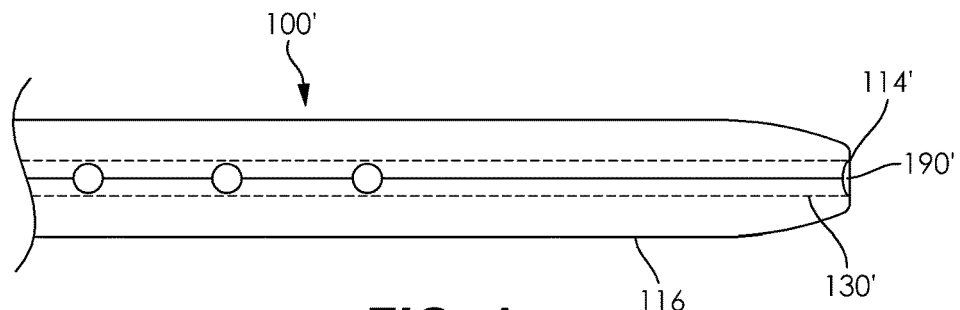
FIG. 4 is a magnified partial view of the distal end of an alternative catheter.

FIG. 4 illustrates an alternative in which the treatment lumen 130' extends from the third opening 124' defined by the elongate member proximal end 112' to a fourth opening 190' defined by the elongate member distal end 114'. This structure is considered advantageous at least because it allows the treatment agent to exit the catheter from the distal end 114' in addition to the plurality of passageways. An opening on the distal end of the catheter, like fourth opening 190' illustrated in FIG. 4, can be included in a catheter according to a particular embodiment in lieu of a passageways, such as the plurality of passageways 140 illustrated in FIG. 1, or in addition to passageways. A skilled artisan can determine whether inclusion of an opening on the distal end is desirable for a catheter according to a particular embodiment based on various considerations, including the nature of the body cavity being treated, any desired peripheral exposure of the treatment agent(s) being used, and other considerations. Also, while the embodiment illustrated in FIGS. 1, 2 and 3 includes a separate cap 160, the embodiment illustrated in FIG. 4 includes an elongate member main body 116' that comprises a unitary member.

Figure 5:
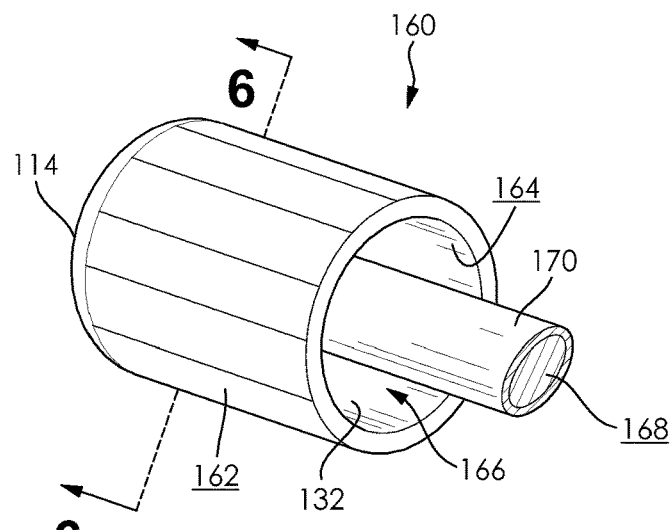
FIG. 5 is a perspective view of the distal cap of the catheter illustrated in FIG. 1.
Figure 6:
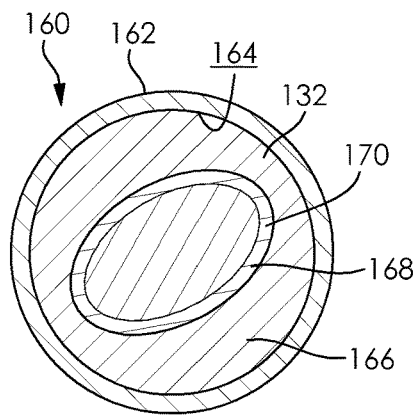
FIG. 6 is a sectional view of the distal cap illustrated in FIG. 5, taken along line 6-6.

In the example catheter illustrated in FIGS. 1 through 3, 5 and 6, the first heating lumen 126 is in fluid communication with the second heating lumen 128. As best illustrated in FIG. 6, a return lumen 132 extends between the first heating lumen 126 and the second heating lumen 128 to provide this fluid communication between the first 126 and second 128 heating lumens. In this example, the treatment lumen 130 terminates proximal to the return lumen 132 along a lengthwise axis of the elongate member 110. As such, the passageway 134 defined by the first heating lumen 126, the return lumen 132, and the second heating lumen 128 extends from the first opening 120 on the elongate member proximal end 112, distally beyond the treatment lumen 130, and to the second opening 122 on the elongate member proximal end 112.

This structure of the passageway 134 allows for a user to introduce an agent, such as a heated fluid, into the passageway at one of the first 120 and second 122 while withdrawing the fluid from the other of the first 120 and second 122 openings. A continual flow of an agent, such as a heated fluid, can be formed in the passageway 134 to permit warming of a treatment agent disposed within the treatment lumen 130, such as a chemotherapeutic agent.

In the example catheter 100, the elongate member main body 116 comprises an elongate shaft 150 attached to a distal cap 160. Each of the first heating lumen 126, the second heating lumen 128, and the treatment lumen 130 extends along the entire axial length of the elongate shaft 150. The distal cap 160 defines the elongate member distal end 114 and is attached to the distal end of the elongate shaft 150. The distal cap 160 defines an external distal cap circumferential wall 162, an internal distal cap circumferential wall 164 that defines an internal distal cap cavity 166, and a terminating surface 168 that, when the distal cap 160 is attached to the elongate shaft 150, seals and terminates the treatment lumen 130. In the illustrated example, the internal distal cap cavity 166 defines return lumen 132 that, when the distal cap 160 is attached to the elongate shaft 150, extends between the first heating lumen 126 and the second heating lumen 128, providing fluid communication between the first heating lumen 126 and the second heating lumen 128.

As best illustrated in FIG. 5, the distal cap 160 defines a plug 170 that extends out of the distal cap cavity 166. The plug 170 has a proximal end that defines the terminating surface 168. When attached to the elongate shaft 150 to form the elongate member main body 116, the plug 170 extends into the distal portion of the treatment lumen to seal and terminate the treatment lumen. In this structural arrangement, the distal cap 160 both seals and terminates the treatment lumen and provides the return lumen 132 that provides fluid communication between the first 126 and second 128 heating lumens.

If included, the distal cap 160 can be attached to the elongate shaft 150 in any suitable manner. Examples of suitable attachments include fixed attachments formed with an adhesive bond between the elongate shaft 150 and the distal cap 160 and a mechanical connection formed between the elongate shaft 150 and the distal cap.

The inclusion of distal cap 160 is considered advantageous at least because it facilitates fabrication of the catheter 100. It is understood, though, that the distal cap 160 is optional and catheters within the scope of the invention can include a unitary elongate member main body that defines the relevant structure, including a suitable return lumen if fluid communication between the first and second heating lumens is desired.

Figure 7:
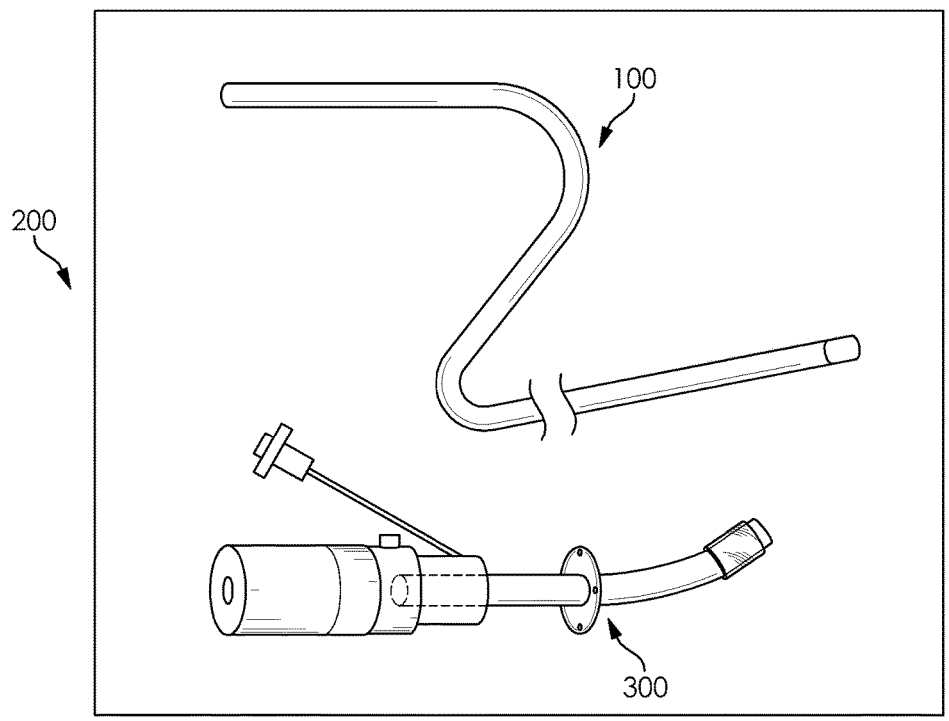
FIG. 7 is a schematic illustration of an example kit including the catheter illustrated in FIG. 1 and an abdominal access port.

FIG. 7 illustrates an example kit 200 useful in the provision of chemotherapeutic treatment, such as the provision of HIPEC and/or EPIC. The kit 200 comprises the catheter 100 illustrated in FIGS. 1 through 3, 5 and 6 and an abdominal access port 300. The abdominal access port 300 can comprise any suitable abdominal access port, including conventional abdominal access ports. The abdominal access port included in a kit according to a particular embodiment need only include suitable structure for engaging opposing surfaces of an abdominal wall and a working lumen through which the catheter 100 can be passed to allow the distal end of the catheter 100 to, ultimately, be disposed within an abdominal cavity of a patient while the proximal end of the catheter 100 remains disposed in an environment external to the abdominal cavity of the patient.

Figure 8:
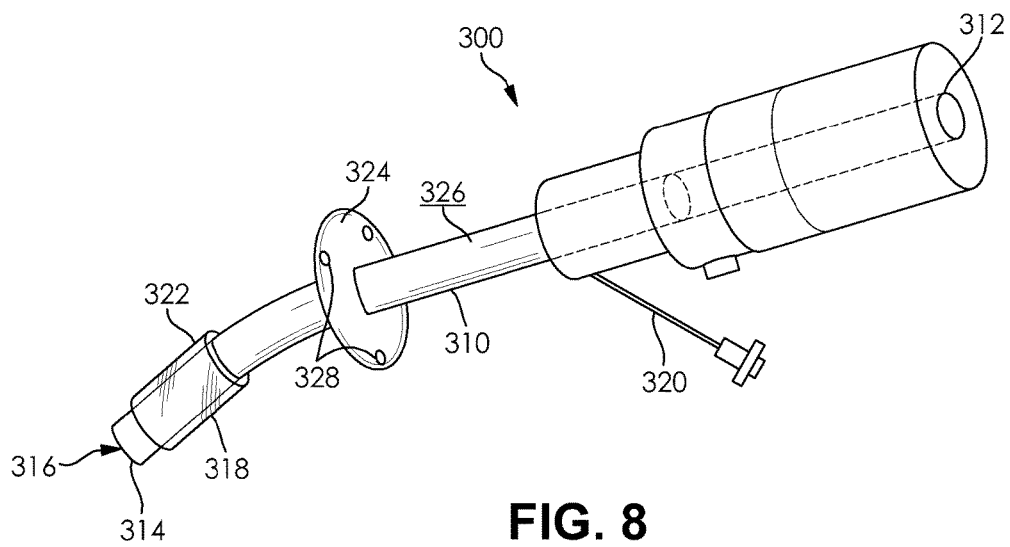
FIG. 8 is a perspective view of the abdominal access port of the kit illustrated in FIG. 7.

FIG. 8 illustrates the abdominal access port 300 independent of the kit 200 and catheter 100. The abdominal access port 300 includes a sheath 310 having a sheath proximal end 312 and a sheath distal end 314. The sheath 310 defines a working lumen 316 through which the catheter 100 can be passed. A balloon 318 is disposed on the sheath near the sheath distal end 314 and is adapted to move between inflated and deflated configurations. An inflation port 320 is in fluid communication with the interior chamber 322 of the balloon 318 such that introduction of fluid into the inflation port 320 moves the balloon 318 from the deflated configuration to the inflated configuration and withdrawal of fluid from the interior chamber 322 of the balloon 318 through the inflation port 320 moves the balloon 318 from the inflated configuration to the deflated configuration.

A sealing disk 324 is disposed on the sheath 310 proximal to the balloon 318 and is movable along the external surface 326 of the sheath 310. The sealing disk 324 includes openings 328 suitable for passing sutures therethrough to facilitate securement of the abdominal access port 300 to skin of a patient during use.

In use, the sheath 310 is passed through an opening in the skin of the patient and into a cavity lying beyond the skin, such as the abdominal cavity. Once the balloon 318 has passed into the cavity but while the sealing disk 324 remains on the other side of the skin, the balloon 318 is inflated by passing fluid through the inflation port 320 and into the interior chamber 322 of the balloon 318. The sheath 310 is then pulled to place the balloon 318, in its inflated configuration, in contact with the interior surface of the cavity. The sealing disk 324 is then moved along the sheath 310, toward the balloon 318, until it contacts the skin, placing the balloon 318, in its inflated configuration, and the sealing disk 324 on opposing sides of the skin of the patient. Sutures can then be passed through the openings 328 of the sealing disk 324 and the skin of the patient to secure the abdominal access port 300 to the patient.

To provide chemotherapeutic treatment to the patient, the catheter 100 can be passed into the working lumen 316 of the sheath 310 such that the distal end 114 of the catheter 100 is finally disposed within the abdominal cavity of the patient. A treatment agent, such as a chemotherapeutic agent, can then be passed into the treatment lumen 130 of the catheter 100 such that it is ultimately introduced into the abdominal cavity of the patient. A fluid that is relatively warmer than the treatment agent can be introduced into the first 126 and/or second 128 heating lumens while the treatment is being performed to warm the treatment agent.

Figure 9:
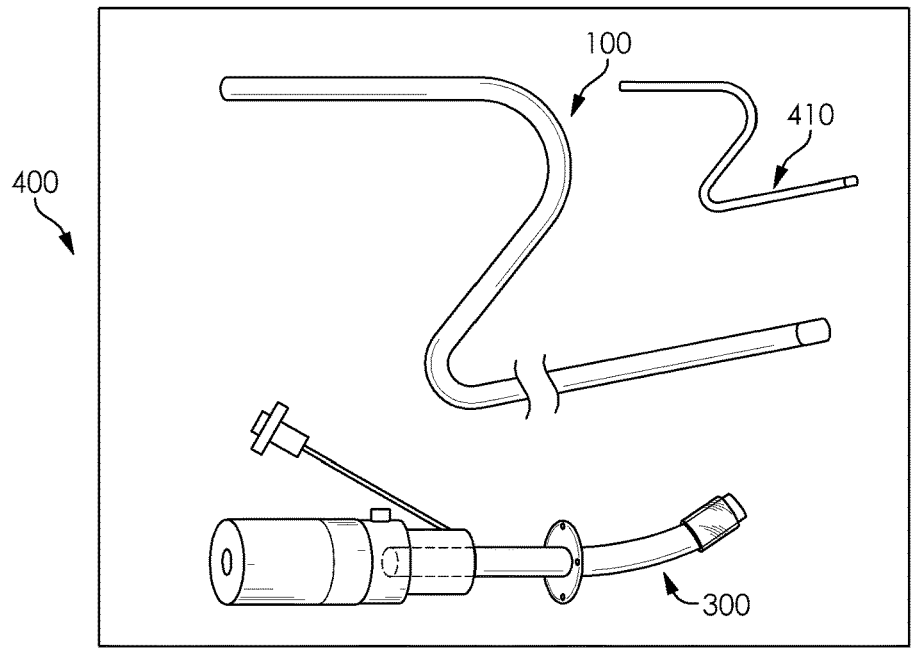
FIG. 9 is a schematic illustration of another example kit including the catheter illustrated in FIG. 1, an abdominal access port, and an additional catheter.

FIG. 9 illustrates another example kit 400 useful in the provision of chemotherapeutic treatment, such as the provision of HIPEC and/or EPIC. The kit 400 comprises the catheter 100 illustrated in FIGS. 1 through 3, 5 and 6, the abdominal access port 300 illustrated in FIGS. 7 and 8, and a second catheter 410. The second catheter 410 can be any suitable catheter, including conventional catheters adapted to deliver a treatment agent to a point of treatment. Examples of suitable types of catheters that can be included as the second catheter 500 include fluid delivery catheters, weeping catheters, catheters with weeping balloons, and the like.

Figure 10:
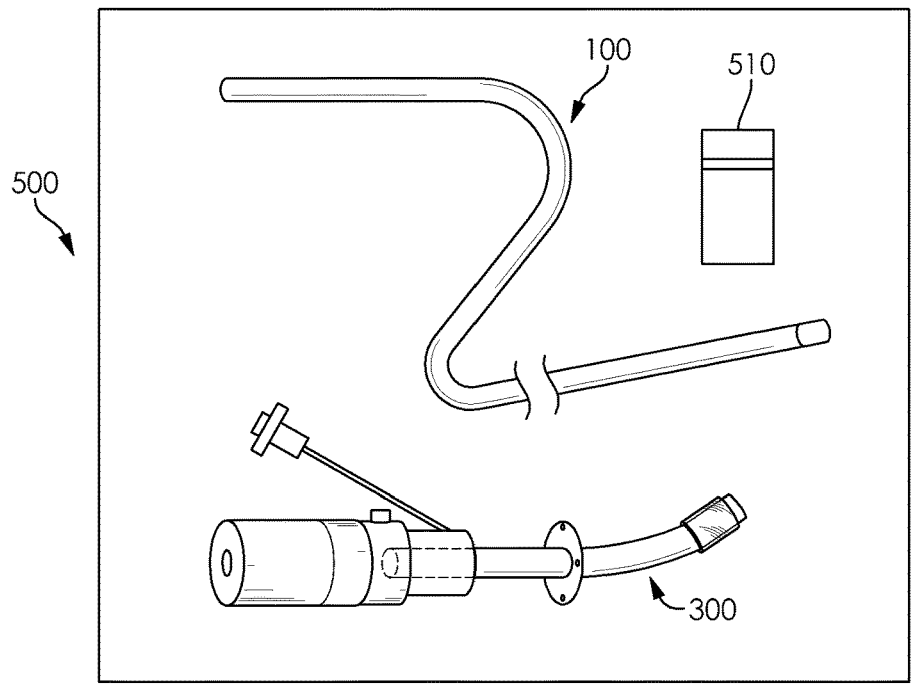
FIG. 10 is a schematic illustration of another example kit including the catheter illustrated in FIG. 1, an abdominal access port, and an additional catheter.

The kit 400 is considered particularly useful in the provision of chemotherapeutic treatment when the second catheter contains halofuginone. These kits are useful in the performance of the methods described below. An alternative kit 500, illustrated in FIG. 10, includes a storage vessel 510, such as a syringe, vial or other suitable storage vessel, containing halofuginone.

Figure 11:
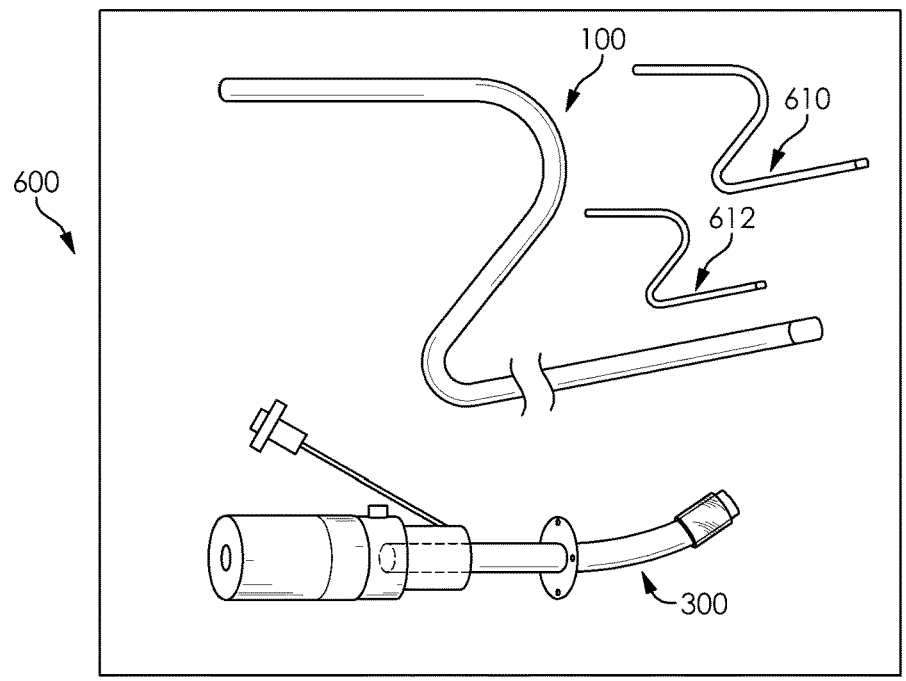
FIG. 11 is a schematic illustration of another example kit including the catheter illustrated in FIG. 1, an abdominal access port, and an additional catheter.

Kits can include one or more additional catheters, such as a catheter adapted to remove fluid from an abdominal cavity of a patient. For example, kit 600, illustrated in FIG. 11, includes a second catheter 610 adapted to remove fluid from an abdominal cavity of a patient and a third catheter 612 adapted to deliver a treatment agent to a point of treatment. The third catheter 612 can contain halofuginone. Alternatively, the kit 600 can comprise a storage vessel containing halofuginone.

Inclusion of halofuginone in a kit, either pre-loaded in a catheter or within a storage vessel, is considered particularly advantageous at least because it facilitates the performance of methods that include pre- and/or post-HIPEC peritoneal infusion of halofuginone.

Figure 12:
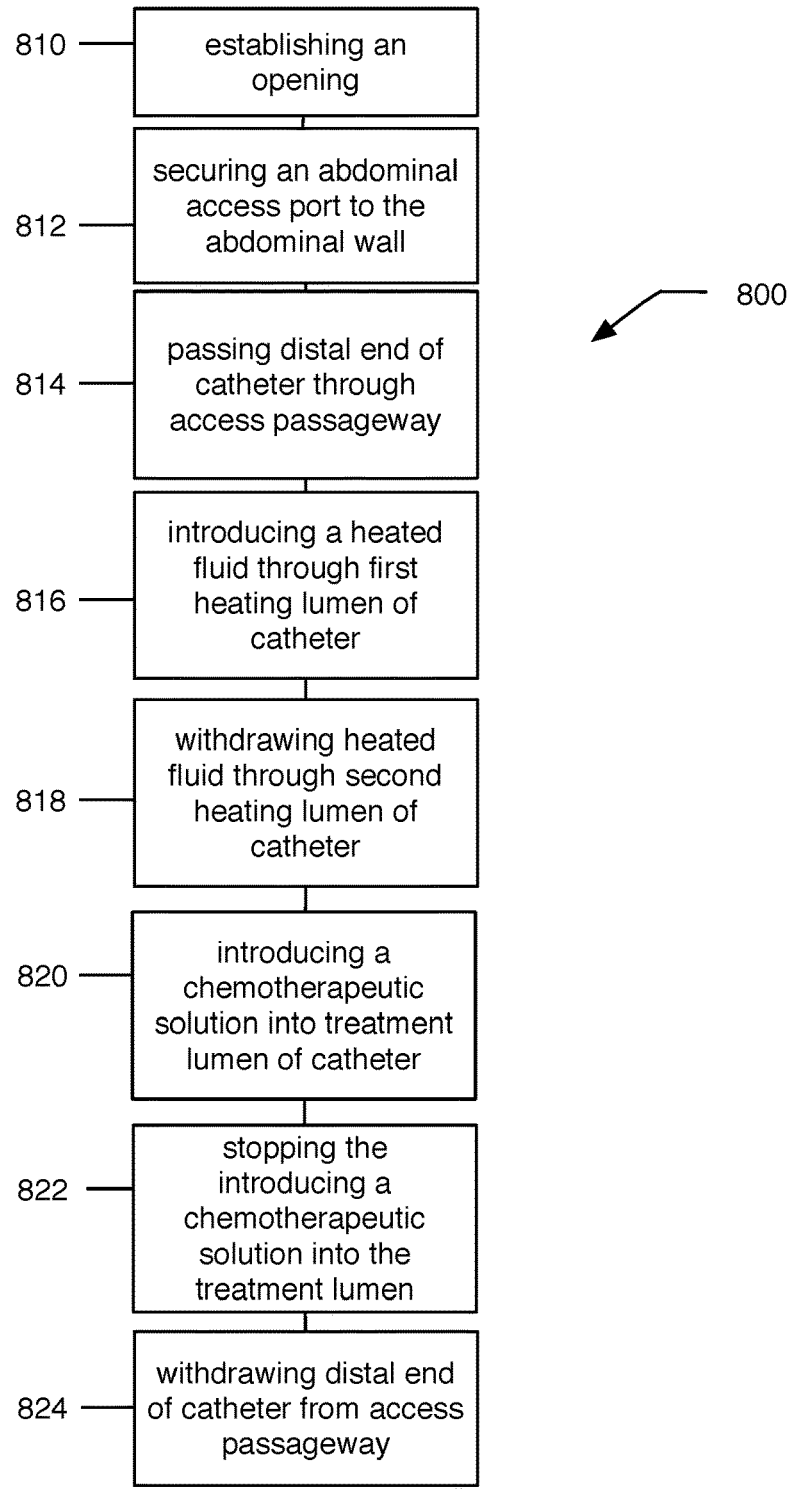
FIG. 12 is a flowchart representation of an example method of providing intraperitoneal chemotherapeutic treatment.

FIG. 12 presents a flowchart illustration of an example method 800 of providing intraperitoneal chemotherapeutic treatment to a patient. An initial step 810 comprises establishing an opening in an abdominal wall of said patient. Another step 812 comprises securing an abdominal access port to the abdominal wall of said patient to establish an access passageway through the opening. Another step 814 comprises passing the distal end of a catheter through the passageway. Another step 816 comprises introducing a heated fluid through the first heating lumen. Another step comprises 818 withdrawing the heated fluid through the second heating lumen. Another step 820 comprises introducing a chemotherapeutic solution into the treatment lumen. Another step 822 comprises stopping the introducing a chemotherapeutic solution into the treatment lumen. Another step 824 comprises withdrawing the distal end of the catheter from the passageway.

In this method, the catheter comprises a catheter according to an embodiment of the invention, such as the catheter 100 illustrated in FIGS. 1 through 3, 5 and 6 and described above.

Figure 13A:
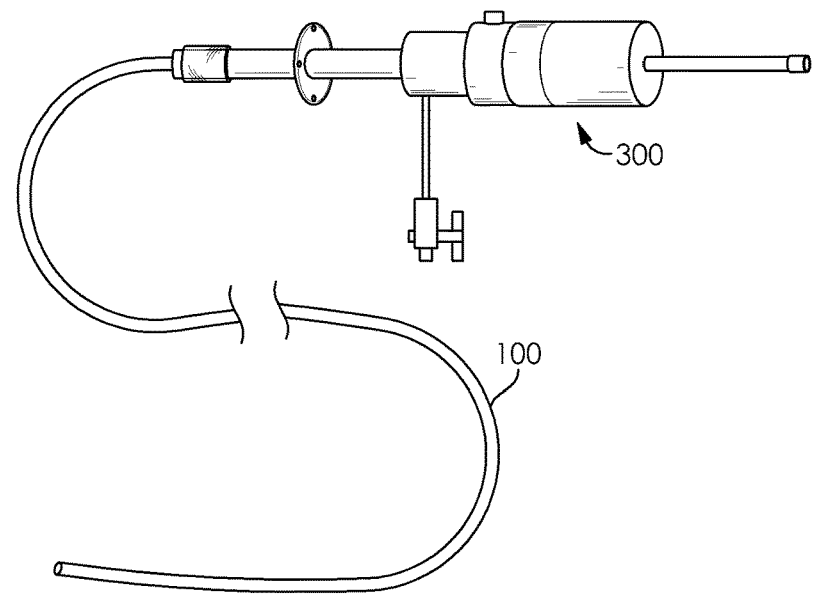
FIG. 13A is a perspective view of a catheter disposed through an abdominal access port during the performance of the method illustrated in FIG. 12.

FIG. 13A is a perspective view of a catheter 100 disposed through an abdominal access port 300 during the performance of the method 800 illustrated in FIG. 12.

Figure 13B:
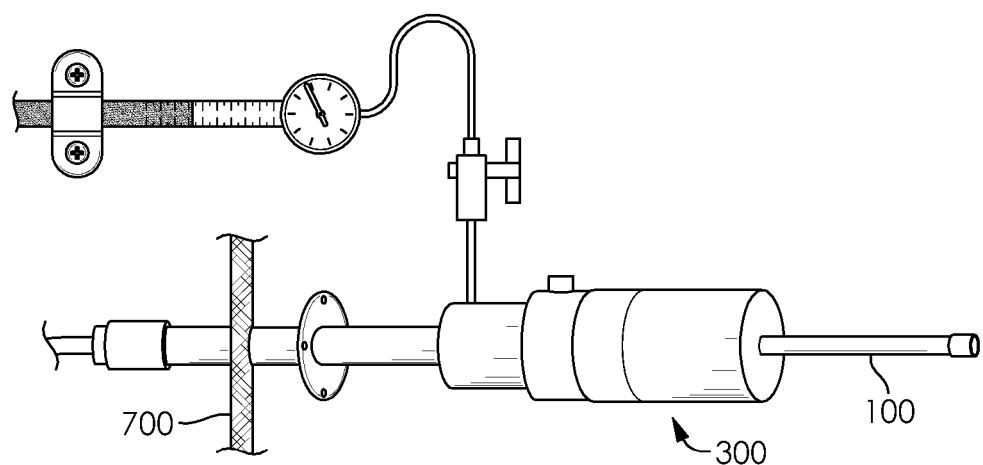
FIG. 13B is a partial perspective view of a patient on which the method illustrated in FIG. 12 is being performed. The abdominal access port is disposed through the abdominal wall and the catheter is disposed through the abdominal access port.

FIG. 13B is a partial perspective view of a patient on which the method 800 illustrated in FIG. 12 is being performed. The abdominal access port 300 is disposed through the abdominal wall 700 and the catheter 100 is disposed through the abdominal access port 300.

Figure 13C:
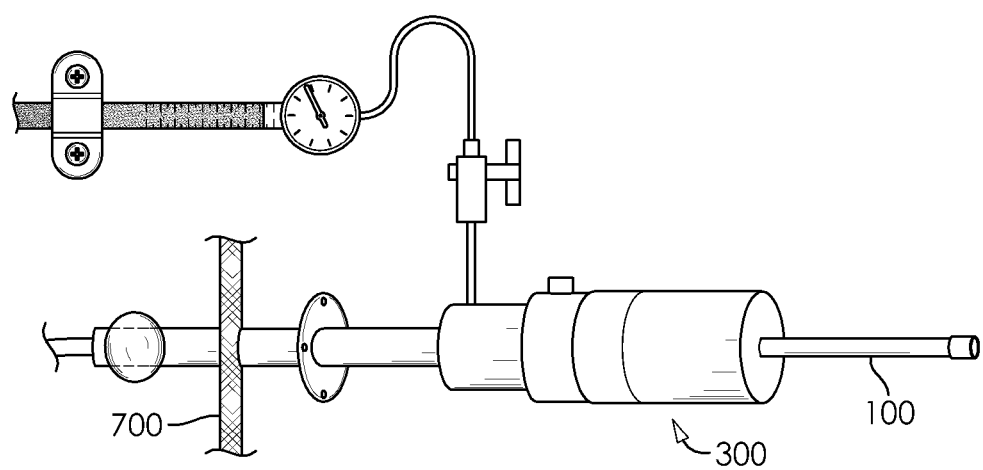
FIG. 13C is a partial perspective view of a patient on which the method illustrated in FIG. 12 is being performed. The abdominal access port is disposed through and secured to the abdominal wall; the catheter is disposed through the abdominal access port.

FIG. 13C is a partial perspective view of a patient on which the method 800 illustrated in FIG. 12 is being performed. The abdominal access port 300 is disposed through and secured to the abdominal wall 700; the catheter 100 is disposed through the abdominal access port 300.

Figure 13D:
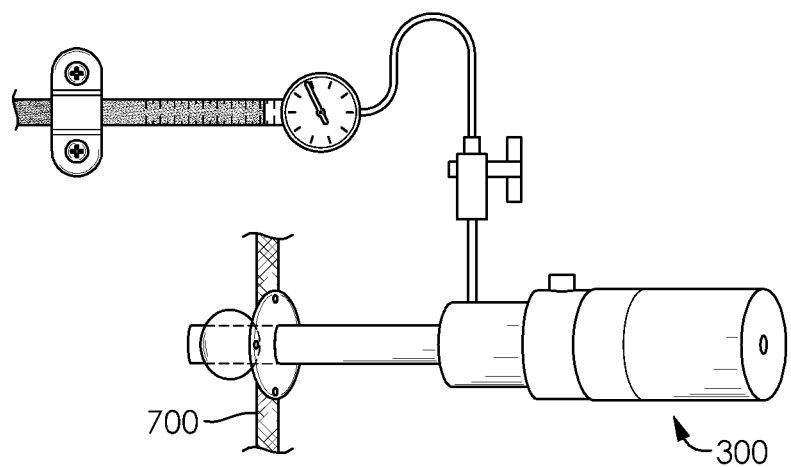
FIG. 13D is a partial perspective view of a patient on which the method illustrated in FIG. 12 is being performed. The abdominal access port is disposed through the abdominal wall; the catheter has been removed.

FIG. 13D is a partial perspective view of a patient on which the method 800 illustrated in FIG. 12 is being performed. The abdominal access port 300 is disposed through the abdominal wall 700; the catheter has been removed.

Figure 13E:
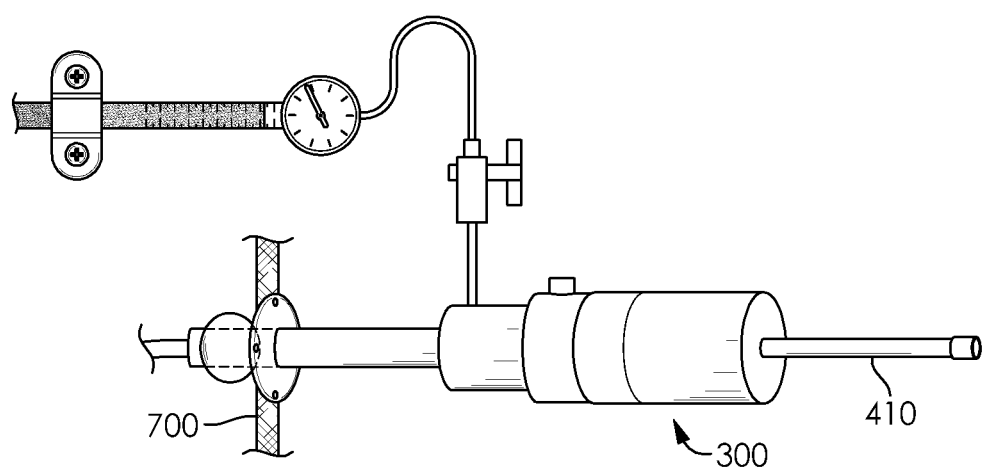
FIG. 13E is a partial perspective view of a patient on which the method illustrated in FIG. 12 is being performed. The abdominal access port is disposed through the abdominal wall and a secondary catheter is disposed through the abdominal access port.

FIG. 13E is a partial perspective view of a patient on which the method 800 illustrated in FIG. 12 is being performed. The abdominal access port 300 is disposed through the abdominal wall 700 and a secondary catheter 410 is disposed through the abdominal access port 300.

Additional methods include steps of infusing halofuginone into the abdominal cavity of the patient. In these methods, the step of infusing halofuginone into the abdominal cavity of the patient can be performed before any of steps 810, 812, 814, 816, 818, 820, 820, and 822 are performed, after all of steps 810, 812, 814, 816, 818, 820, 820, and 822 are performed, or while one or more of steps 810, 812, 814, 816, 818, 820, 820, and 822 are performed.

Figure 14:
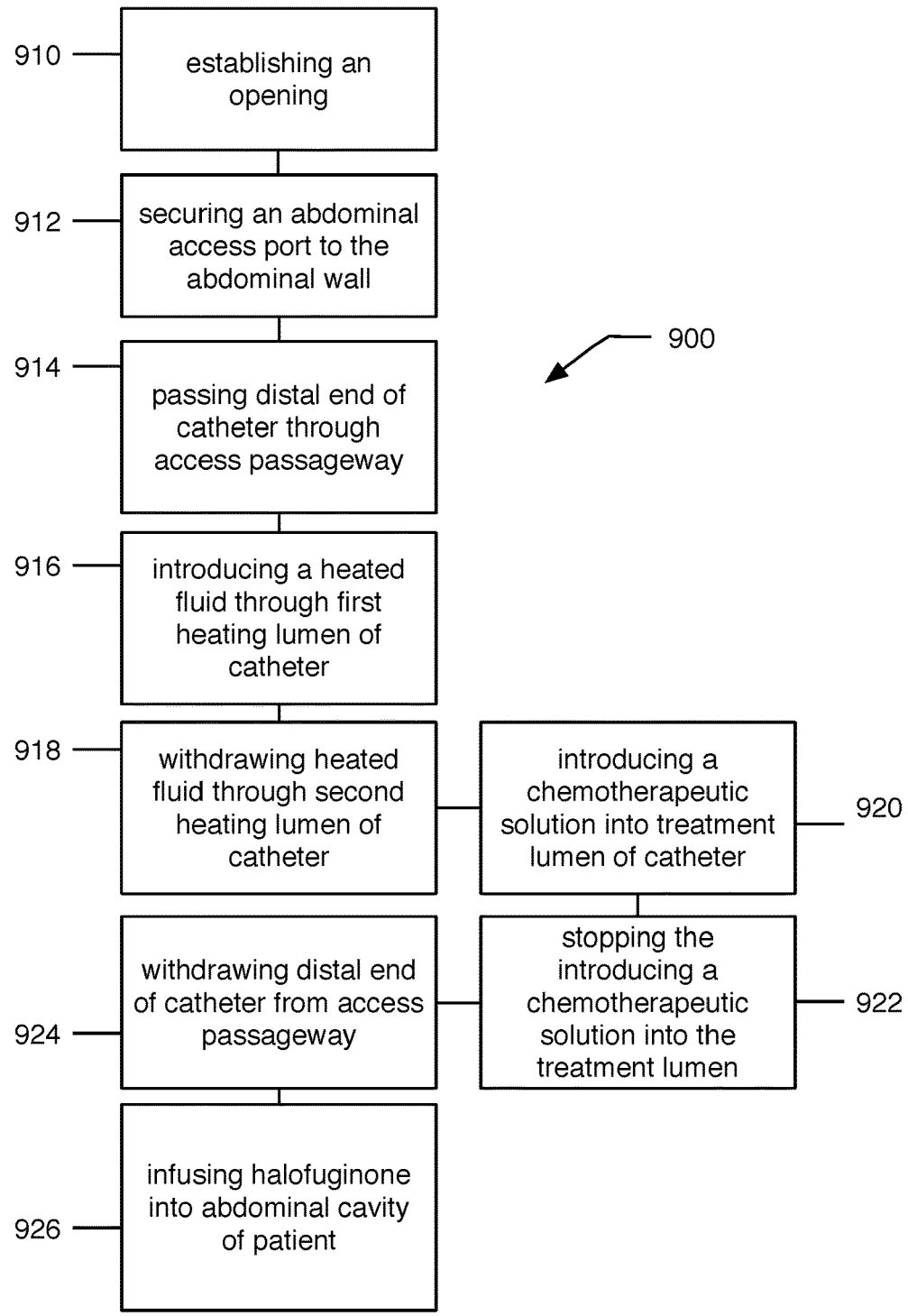
FIG. 14 is a flowchart representation of another example method of providing intraperitoneal chemotherapeutic treatment.

For example, FIG. 14 illustrates an example method 900 of providing intraperitoneal chemotherapeutic treatment to a patient in which a step 926 of infusing halofuginone into the abdominal cavity of the patient is performed after all other steps have been performed. In this method 900, an initial step 910 comprises establishing an opening in an abdominal wall of said patient. Another step 912 comprises securing an abdominal access port to the abdominal wall of said patient to establish an access passageway through the opening. Another step 914 comprises passing the distal end of a catheter through the passageway. Another step 916 comprises introducing a heated fluid through the first heating lumen. Another step 918 comprises withdrawing the heated fluid through the second heating lumen. Another step 920 comprises introducing a chemotherapeutic solution into the treatment lumen. Another step 922 comprises stopping the introducing a chemotherapeutic solution into the treatment lumen. Another step 924 comprises withdrawing the distal end of the catheter from the passageway. Another step 926 comprises infusing halofuginone into the abdominal cavity of the patient after all other steps of the method 900 have been performed.

While the example medical devices, kits and methods described herein are described in connection with the provision of HIPEC and/or EPIC to a patient, it is noted that medical devices, kits and methods according to the invention, including the examples described herein, may be useful in connection with the provision of other treatments.

While the examples described above reference specific features of particular drawings, it is understood that the various elements and/or features described herein in connection with one particular embodiment can be combined with those of another without departing from the scope of the invention. Furthermore, the catheters, kits and methods described and illustrated herein are examples. As such, they are not intended to limit the scope of protection sought in any manner. Rather, they serve only to aid those skilled in the art to make and use apparatuses and to practice methods in accordance with the invention.

What is claimed is:

1. A catheter, comprising:
    an elongate member having an elongate member proximal end, an elongate member distal end, and an elongate member main body extending between the elongate member proximal end and the elongate member distal end, the elongate member main body defining an elongate member circumferential wall, first, second, and third openings on the elongate member proximal end, a first heating lumen extending from the first opening toward the elongate member distal end, a second heating lumen extending from the second opening toward the elongate member distal end, and a treatment lumen extending from the third opening toward the elongate member distal end; and
    a distal cap disposed on the distal end of the elongate member, the distal cap defining a terminating surface that terminates the treatment lumen and a return lumen extending and providing fluid communication between the first heating lumen and the second heating lumen;
    wherein the treatment lumen comprises a blind passage and the elongate member circumferential wall defines a plurality of passageways providing fluid communication between the treatment lumen and an environment external to said catheter.

2. The catheter of claim 1, wherein the first heating lumen is in fluid communication with the second heating lumen.

3. The catheter of claim 2, wherein the elongate member main body defines a return lumen extending between the first heating lumen and the second heating lumen.

4. The catheter of claim 3, wherein the treatment lumen terminates proximal to the return lumen along a lengthwise axis of the elongate member.

5. A catheter, comprising:
    an elongate member having an elongate member proximal end, an elongate member distal end, and an elongate member main body extending between the elongate member proximal end and the elongate member distal end, the elongate member main body defining an elongate member circumferential wall, first, second, and third openings on the elongate member proximal end, a first heating lumen extending from the first opening toward the elongate member distal end, a second heating lumen extending from the second opening toward the elongate member distal end, and a treatment lumen extending from the third opening toward the elongate member distal end;
    the elongate member circumferential wall defining a plurality of passageways providing fluid communication between the treatment lumen and an environment external to said catheter; and
    a distal cap disposed on the distal end of the elongate member, the distal cap defining a return lumen and a proximally-extending plug, the return lumen extending and providing fluid communication between the first heating lumen and the second heating lumen and the proximally-extending plug extending into the treatment lumen.

6. The catheter of claim 5, wherein the distal cap comprises a separate member attached to the elongate member.

7. The catheter of claim 5, wherein the proximally-extending plug defines a terminating surface disposed within the treatment lumen.

8. The catheter of claim 5, wherein the distal cap defines a distally-extending cavity that defines the return lumen.

9. The catheter of claim 5, wherein the treatment lumen is disposed between the first and second heating lumens along a lengthwise axis of the elongate member.

10. The catheter of claim 9, wherein the treatment lumen has a generally ovoid cross-sectional shape.

11. The catheter of claim 10, wherein each of the first and second heating lumens has a semi-ovoid cross-sectional shape.

* * * * *